(12) United States Patent  (10) Patent No.: US 7,896,704 B2
Stafford et al.  (45) Date of Patent: Mar. 1, 2011

(54) STRIP CONNECTORS FOR MEASUREMENT DEVICES

(75) Inventors: Gary Ashley Stafford, Hayward, CA (US); Richard G. Ries, Livermore, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 12/624,231

(22) Filed: Nov. 23, 2009

(65) Prior Publication Data

US 2010/0065426 A1  Mar. 18, 2010

Related U.S. Application Data

(63) Continuation of application No. 12/175,279, filed on Jul. 17, 2008.

(51) Int. Cl.
  *H01R 25/00* (2006.01)
(52) U.S. Cl. .......................... 439/638; 439/909; 439/606
(58) Field of Classification Search .................. 439/604, 439/606, 638, 722, 723, 724, 874, 909
  See application file for complete search history.

(56) References Cited

U.S. PATENT DOCUMENTS

| | | | |
|---|---|---|---|
| 4,150,863 A | 4/1979 | Krafthefer et al. |
| 4,494,809 A | 1/1985 | Soloman |
| 4,533,202 A | 8/1985 | Pohl |
| 4,545,382 A | 10/1985 | Higgins et al. |
| 4,711,245 A | 12/1987 | Higgins et al. |
| 4,774,192 A | 9/1988 | Terminiello et al. |
| 4,911,344 A | 3/1990 | Kahler |
| 4,940,422 A | 7/1990 | Forish et al. |
| 5,217,388 A | 6/1993 | Brown |
| 5,279,294 A | 1/1994 | Anderson et al. |
| 5,391,094 A | 2/1995 | Kakinoki et al. |
| 5,509,410 A | 4/1996 | Hill et al. |
| 5,526,120 A | 6/1996 | Jina et al. |
| 5,593,323 A | 1/1997 | Dernehl |
| 5,628,890 A | 5/1997 | Carter et al. |
| 5,708,247 A | 1/1998 | McAleer et al. |
| 5,820,551 A | 10/1998 | Hill et al. |
| 5,984,690 A | 11/1999 | Riechelmann et al. |
| 6,071,391 A | 6/2000 | Gotoh et al. |
| 6,120,676 A | 9/2000 | Heller et al. |
| 6,143,164 A | 11/2000 | Heller et al. |
| 6,175,752 B1 | 1/2001 | Say et al. |
| 6,183,274 B1 | 2/2001 | Allum |
| 6,268,162 B1 | 7/2001 | Phillips et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,431,884 B1 | 8/2002 | Wallace et al. |
| 6,445,350 B2 | 9/2002 | Takenobu |

(Continued)

FOREIGN PATENT DOCUMENTS

DE  202006013075 U1  11/2006

(Continued)

*Primary Examiner*—Tho D Ta
(74) *Attorney, Agent, or Firm*—Edward J. Baba; Peter A. Socarras; Bozicevic, Field & Francis LLP

(57) ABSTRACT

Devices including strip connectors in measurement devices are provided. Also provided are systems, kits and methods.

64 Claims, 4 Drawing Sheets

U.S. PATENT DOCUMENTS

| | | |
|---|---|---|
| 6,461,496 B1 | 10/2002 | Feldman et al. |
| 6,503,381 B1 | 1/2003 | Gotoh et al. |
| 6,506,168 B1 | 1/2003 | Fathallah et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,616,819 B1 | 9/2003 | Liamos et al. |
| 6,618,934 B1 | 9/2003 | Feldman et al. |
| 6,676,816 B2 | 1/2004 | Mao et al. |
| 6,679,137 B1 | 1/2004 | Bek |
| 6,730,200 B1 | 5/2004 | Stewart et al. |
| 6,736,957 B1 | 5/2004 | Forrow et al. |
| 6,743,635 B2 | 6/2004 | Neel et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,850,283 B1 | 2/2005 | Tatamiya |
| 6,881,578 B2 | 4/2005 | Otake |
| 6,893,545 B2 | 5/2005 | Gotoh et al. |
| 6,908,008 B2 | 6/2005 | Pugh |
| 6,940,021 B2 | 9/2005 | Pohl et al. |
| 6,942,518 B2 | 9/2005 | Liamos et al. |
| 6,976,624 B2 | 12/2005 | Hsiao |
| 7,041,468 B2 | 5/2006 | Drucker et al. |
| 7,172,728 B2 | 2/2007 | Otake |
| 7,179,129 B1 | 2/2007 | Hwang |
| 7,337,918 B2 | 3/2008 | Fowler et al. |
| 7,488,216 B2 * | 2/2009 | Cho .......................... 439/638 |
| 2003/0191415 A1 | 10/2003 | Moerman et al. |
| 2004/0073095 A1 | 4/2004 | Causey et al. |
| 2004/0086425 A1 | 5/2004 | Jaunakais |
| 2004/0094433 A1 | 5/2004 | Neel et al. |
| 2004/0267300 A1 | 12/2004 | Mace |
| 2005/0121826 A1 | 6/2005 | Hajizadeh et al. |
| 2005/0154271 A1 | 7/2005 | Rasdal et al. |
| 2005/0169810 A1 | 8/2005 | Hagen et al. |
| 2005/0281706 A1 | 12/2005 | Funke et al. |
| 2006/0040333 A1 | 2/2006 | Zocchi |
| 2006/0148096 A1 | 7/2006 | Jina |
| 2007/0100222 A1 | 5/2007 | Mastrototaro et al. |
| 2007/0247793 A1 | 10/2007 | Carnevali |
| 2008/0099332 A1 | 5/2008 | Scott et al. |
| 2008/0234559 A1 | 9/2008 | Arbogast et al. |

FOREIGN PATENT DOCUMENTS

| | | |
|---|---|---|
| EP | 1112717 A1 | 7/2001 |
| EP | 1543935 A2 | 6/2005 |
| EP | 1712910 A1 | 10/2006 |
| EP | 1729128 A1 | 12/2006 |
| FR | 2674379 A1 | 9/1992 |
| GB | 1170256 A | 11/1969 |
| WO | WO 2005/096446 A1 | 10/2005 |
| WO | WO 2006/002432 | 1/2006 |
| WO | WO 2007/097746 A1 | 8/2007 |

* cited by examiner

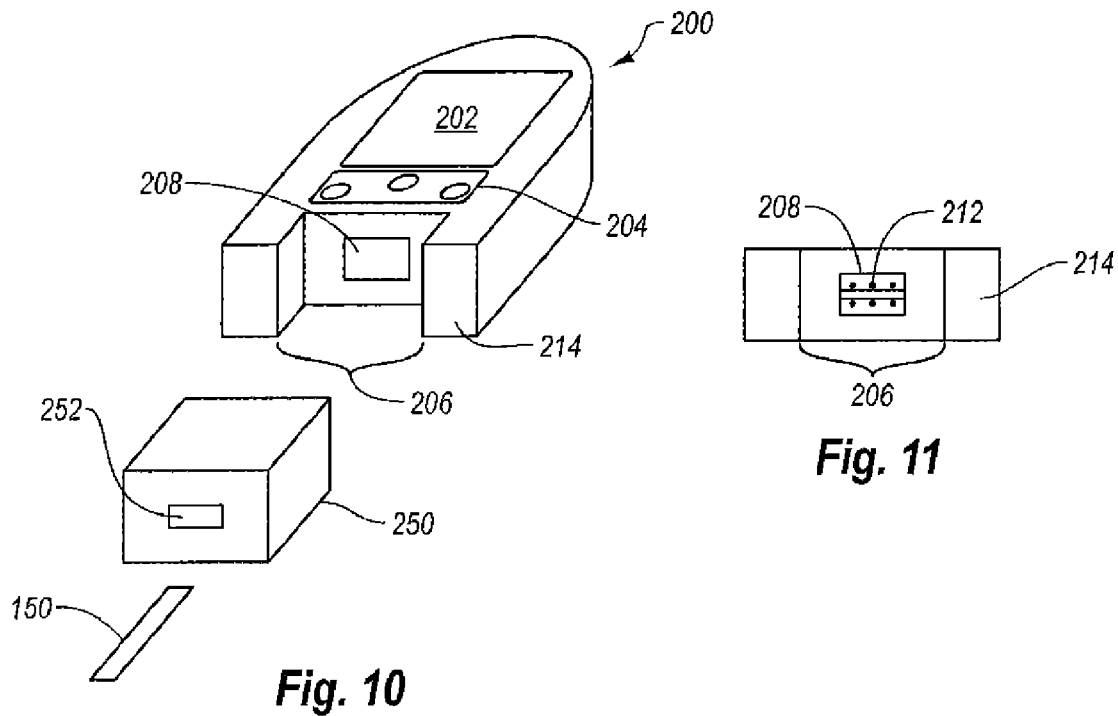
Fig. 10
Fig. 11
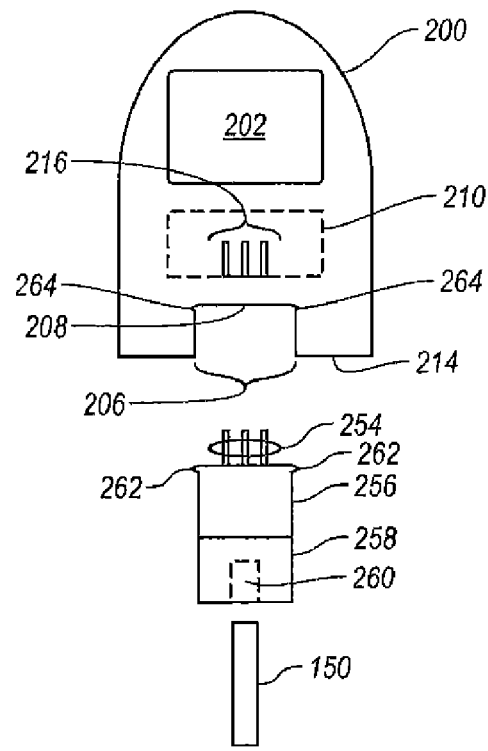
Fig. 12

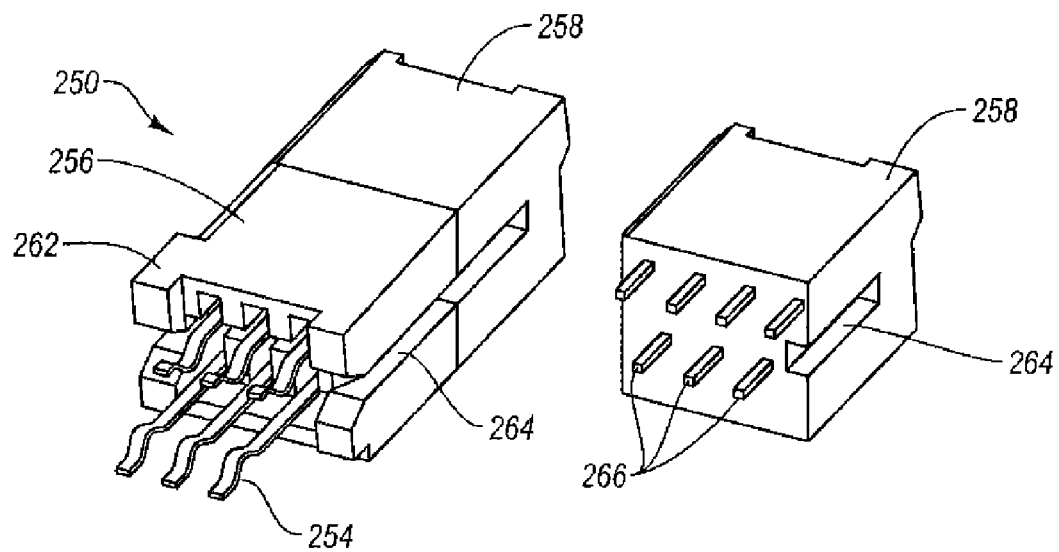
Fig. 13  Fig. 14
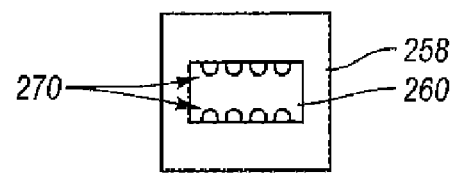
Fig. 15
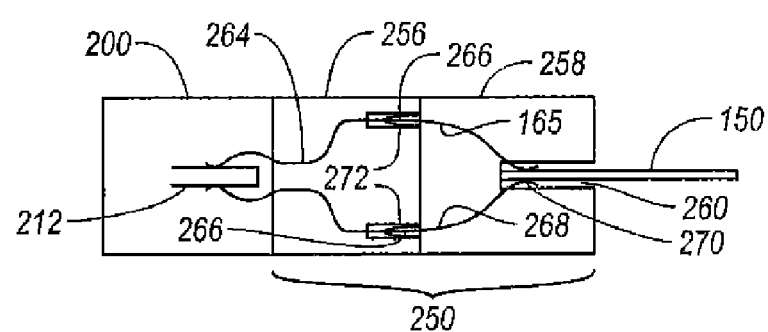
Fig. 16

STRIP CONNECTORS FOR MEASUREMENT DEVICES

CROSS-REFERENCE TO RELATED APPLICATIONS

Not applicable.

BACKGROUND OF THE INVENTION

1. The Field of the Invention

Embodiments of the invention relate to strip connectors in measurement devices. More particularly, embodiments of the invention relate to strip connectors for use with measurement devices that are substantially impervious to liquid or other contaminants or that are replaceable or disposable.

2. The Relevant Technology

Diabetes is a disease that afflicts many people. One of the tools used in diabetes management is a measurement device, whose primary purpose is to measure the blood glucose level of a person from a sample of blood. The process of using a measurement device is not overly complicated and it is often performed several times a day.

After inserting a test strip into a port of the measurement device, a user may lance his or her finger to obtain a small sample of blood. The blood sample is then placed onto the test strip and the measurement device analyzes the blood sample. The measurement device typically displays a blood glucose level from the analysis.

In order to ensure that an accurate measurement is being generated, it is necessary to keep the measurement device free from contamination. There are instances where the port becomes contaminated with blood, for example. When this occurs, the performance of the measurement device suffers and the user is no longer assured of an accurate result. As a result, the user is likely required to purchase a new measurement device. A user can be inconvenienced because of the inaccurate results and the need to purchase a new device.

BRIEF SUMMARY OF THE INVENTION

Embodiments of the present invention relate to strip connectors on measurement devices or for use with measurement devices. Embodiments of the invention include strip ports that are corrosion resistant, washable, impervious to liquid ingress, dust proof, conductive, and/or replaceable. In one embodiment, the measurement device includes a case that has a first end. A strip connector may be disposed in the first end or other portion of the case. The strip port includes contacts that extend out from the first end. The case may be formed such that an interface between the case and the contacts forms a barrier that is substantially impervious to liquids. The interface allows the strip connector and the contacts to be cleaned and allows the contacts to be kept free from contaminants. This extends the mean time before failure (MTBF) of the device because the strip connector can be cleaned.

In certain embodiments, the port is configured to be replaceable. In this example, the device includes a receptacle for receiving the port. The port may include a first portion having a first electrical interface. The first electrical interface is typically configured to interface with the device. The first portion of the device also includes a second electrical interface.

The port may also include a second portion. A third electrical interface may be configured to detachably and electrically connect with the second electrical interface. This allows the second portion to be removed from the first portion and replaced if contaminated or for any other reason. The second portion also includes a strip port configured to receive a test strip. The port then provides an electrical and physical connection between the measurement device and the test strip.

A disposable port or a port with a disposable portion also increases the MTBF of the device. Also, a disposable port allows the second portion to be selected to accommodate different test strip form factors.

These and other advantages and features of the present invention will become more fully apparent from the following description and appended claims, or may be learned by the practice of the invention as set forth hereinafter.

BRIEF DESCRIPTION OF THE DRAWINGS

To further clarify the advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 10 illustrates a perspective view of a device that uses a disposable strip port;

FIG. 11 illustrates a side view of an end of the device including the electrical interface that receives the disposable port;

FIG. 12 illustrates a top view of a disposable port that interfaces with a device and with a test strip;

FIG. 13 is a perspective view of a disposable port that includes a separable portions such that one portion interfaces with the measurement device and another portion interfaces with a test strip;

FIG. 14 illustrates a perspective view of one embodiment of a portion of the disposable port that provides an electrical interface for a test strip;

FIG. 15 illustrates an end view of the disposable port including the test strip interface;

FIG. 16 illustrates electrical connections between the device and the test strip through the disposable port.

DETAILED DESCRIPTION

Embodiments of the invention relate to electrical interfaces in measurement devices. Measurement devices often have electrical interfaces that allow them to electrically connect with another device or apparatus and perform an analysis of an analyte. A device that measures blood glucose levels, for example, includes electrical interfaces that allow the device to measure the blood glucose level from a small blood sample.

Embodiments of the invention relate to systems and methods that can improve the mean time before failure (MTBF) in measurement devices. This has the benefit of providing a user with a device that lasts longer and also ensures that the measurements or analysis performed by the device are more accurate over time.

More specifically, embodiments of the invention relate to strip connectors or strip ports that can be cleaned and/or replaced. The ability to clean or replace a strip port can prevent the device from experiencing problems often associated with port contamination. Blood and other contaminants, for example, can often contaminate a port and make the device unusable or result in inaccurate analysis. A port that can be cleaned or replaced without affecting the operation of the device thus increases the MTBF.

One embodiment thus relates to an insert molded strip connector configuration that prevents the ingress of liquid or other contaminant. The molded strip connector can be corrosion resistant, washable, water proof, dust proof, and highly electrically conductive. In another embodiment the port or at least a portion of the port is disposable. A disposable port allows the device to adapt to different test strip form factors by selecting the appropriate port replacement and also allows the device to continue to function when the port is contaminated by simply replacing the contaminated port.

Figure 1:
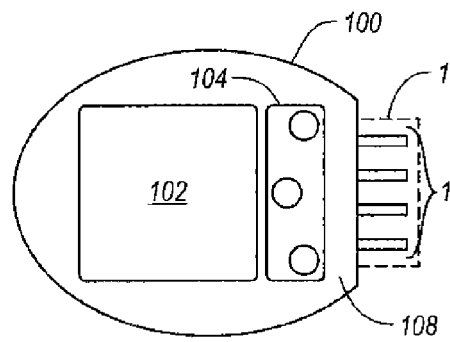
FIG. 1 illustrates a view of a measurement device including a strip connector that makes the strip interface cleanable.

FIG. 1 illustrates a top view of one embodiment of a measurement device used to analyze an analyte. The measurement device 100 typically includes a display 102 and a user interface 104. The display 102 can be used to provide instructions or results to the user related to the measurement of the blood glucose level in a sample of blood. The user interface 104 allows a user to perform various functions, including starting the analysis, turning the device on/off, and the like.

Figure 2:
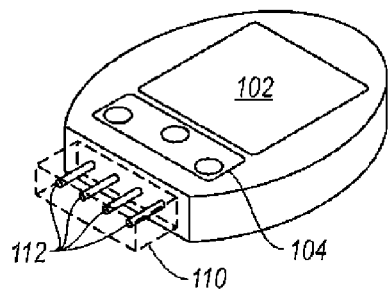
FIG. 2 illustrates a perspective view of a measurement device with a strip connector.

FIGS. 1 and 2 also illustrate an example of a strip connector 110. The strip connector 110, in this example, includes a plurality of contacts 112. The contacts 112 provide a physical and/or electrical interface to an appropriately configured test strip or test strip module. In this example, the case 108 of the device 100 may be molded around the contacts 112. By molding the case 108 of the device 110 around the contacts, the interface between the case 108 and the contacts 112 becomes impervious to contamination, including liquid contamination (e.g., water, blood, etc.). The interface between the case 108 and the contacts 112 then becomes waterproof or at least sufficiently waterproof to allow the device 100 or at least the strip connector 110 to be washed. The ability to wash the device 100 or at least the strip connector 110 makes the device 100 substantially or completely corrosion resistant, washable, waterproof and dustproof. Contaminants can be removed or cleaned from the device without affecting the device 100.

The contacts 112 are usually conductive and may be gold plated to improve the conductivity of the contacts 112. The contacts 112 may also be formed of high strength steel to protect the contacts, which are exposed and extend out of the case 108 of the device 100. In other embodiments, the contacts may be formed from impregnated polymers, beryllium copper, phosphor bronze, titanium, nickel plated, tin plated or any combination thereof. In alternative embodiments, the contacts may be any material that provides the proper conductivity where necessary.

The contacts 112 can be arranged in a plurality of different configurations. The contacts can be arranged in one or more rows and/or columns on the surface 120. The contacts 112 can be arranged to connect with different sides of the printed circuit board (or other connector) inside the device 100. Further, the contacts 112 can be bent or shaped to connect with a test strip and provide the electrical and/or mechanical connection between the device 100 and the test strip. As discussed more fully herein the device 100 can be configured with various types of contacts that permit the device to interface with test strips of different form factors. In addition, other structures may extend out of the surface 120 to provide mechanical structure to secure the test strip.

Figure 3:
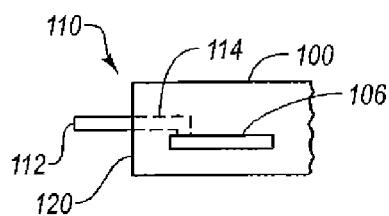
FIG. 3 illustrates one embodiment of contacts included in a strip connector.

FIG. 3 illustrates a side view of a device 100 including the strip port 110. In this example, the strip port 110 extends out of the device 100 through the surface 120 and the interface between the surface 120 and the contacts 112 is sealed or substantially sealed to prevent ingress of liquid or other contaminant. The contacts 112 typically pass through the surface 120 of the device 100 and include a connector 114 to the printed circuit board 106. The connector 114 may be a bond wire or other connection to form a conductive path between the printed circuit board 106 and the contacts 112. The contacts 112, in this embodiment, are pin type contacts.

Figures 4, 5:
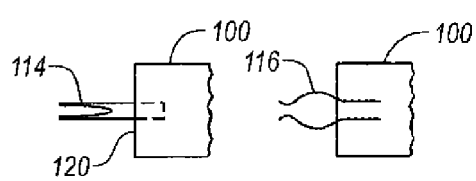
FIG. 4 illustrates another embodiment of contacts included in a strip connector.
FIG. 5 illustrates another embodiment of contacts included in a strip connector.

FIGS. 4 and 5 illustrate additional embodiments of the contacts 112. FIG. 4 illustrates a clip pin 114 while the contact depicted in FIG. 5 is a spring arm 116. Each type of contact 112 enables physical and/or electrical contact with a corresponding test strip in a different way and may accommodate different form factors. In each example, the contacts 112 pass through the surface 120 of the device 100 and electrically connect with a printed circuit board or other circuitry inside the device. The surface 120 has been formed around the contacts 112 to provide a barrier that allows the contacts 112 to be cleaned or washed.

Figure 6:
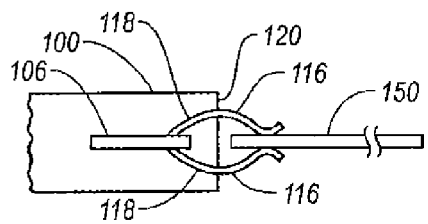
FIG. 6 illustrates a device with spring arm connectors connected with a test strip.

FIG. 6 illustrates a side view of the device 100 connected with a test strip 150. In this example, the device 100 includes spring arms 116 that extend out of the surface 120. When the strip 150 is inserted into the spring arms 116, the spring arms 116 may separate and exert a force towards the test strip 150 to hold the test strip in place physically and to provide an electrical connection between the spring arms 116 and the test strip 150. In FIG. 6, the portion 118 of the spring arms 116 inside the device 100 connect with the printed circuit board 106 on both sides in this example, although there is no requirement that each portion of each of the spring arms 116 or of the contacts in general be used to establish an electrical connection.

The case 108 of the device 100 has been formed, such as by injection molding, to form a surface 120 that encloses the portion 118 of the spring arms 116 (or other contact) inside of the device 100 while exposing the external portion of the spring arms 116 (or other contact). As a result, the interface between the spring arms 116 and the surface 120 is sealed or substantially sealed to prevent ingress of liquid such as blood or other contaminant from entering the device 100 and interfering with the operation or functionality of the device 100. As a result of this interface, the spring arms 116 or other contact can be washed or cleaned in the event of contamination or for any other reason without interfering with the operation of the device 100.

Figure 7:
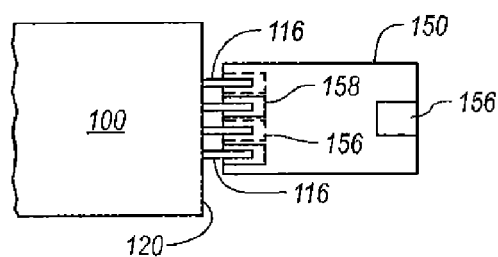
FIG. 7 illustrates a top view of a device with contacts that is electrically connected with a test strip.

FIG. 7 illustrates a top view of the device 100 illustrated in FIG. 6. In this example, the spring arms 116 extend out of the surface 120 and are connected to the test strip 150. A blood sample 156 is loaded on the test strip and contacts 156 and 158 are in contact with the spring arms 116. In this example, the contact 158 is on one side of the test strip 150 while the contact 156 is on the other side of the test strip 150. The spring arm configuration illustrated in FIG. 7 enable contacts 158 and 156 of the test strip 150 to be on either side of the test strip. In some instances, some of the spring arms 116 may not be in electrical contact with the test strip 150.

Figure 8:
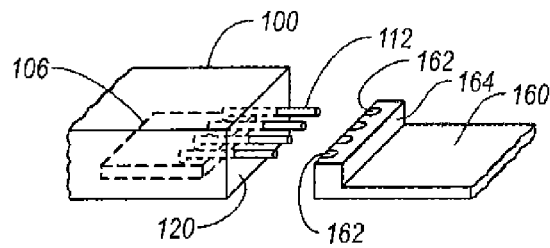
FIG. 8 illustrates another embodiment of a device with pin contacts that interface with corresponding sockets on a test strip.

FIG. 8 depicts a perspective view of another embodiment of a molded strip connector. In this example, the device 100 includes pin contacts 112 that pass through a surface 120 of the device 100. At least some of the pin contacts 112 encased or enclosed within the case 108 of the device 100 are electrically connected to the printed circuit board 106. Because the contact pins 112 can be arranged in various configurations, such as rows and columns, the pin contacts 112 can connect to both sides of the printed circuit board 106.

The test strip 160 illustrated in FIG. 8 includes sockets 162 that are shaped and configured to cooperate with the pin contacts 112 to establish at least an electrical connection, but may also provide physical stability to the connection between the test strip 160 and the device 100. The sockets 162 are mounted in a connection module 164 that routes the electrical connection of the sockets 162 to the strip 160 such that the device 100 can analyze any analyte located thereon.

Figure 9:
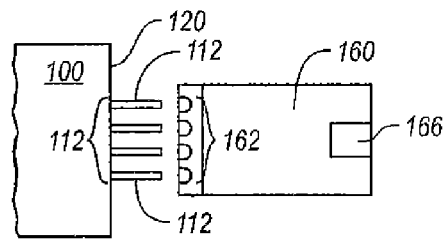
FIG. 9 illustrates a top view of pin contacts in a strip connector.

FIG. 9 illustrates a top view a device with a test strip port. FIG. 9 illustrates that the contacts 112 can be inserted into the sockets 162 to form a connection between the device 100 and the test strip 160. When a sample is loaded in the space 166, the connection established between the device 100 and the test strip 160 via the pin contact/socket connection, the sample can be analyzed.

Another embodiment of the invention relates to a disposable strip port. A disposable strip port enables the port or a portion thereof to be exchanged, by way of example and not limitation, for another port or portion thereof when the current port or portion thereof malfunctions or is contaminated. FIG. 10 illustrates a perspective view of a measurement device 200. The device 200 includes a display 202 and a user interface similar to the display and user interface illustrated in FIG. 1. The display 202 may be used to convey information including results (such as blood glucose level) on an analysis of an analyte such as a blood sample.

The device 200 includes a port 208 that is inset in a receptacle 206 formed in the device 200. The receptacle 206 can be configured to receive a disposable or replaceable port 250. As illustrated in FIG. 10, the disposable port 250 can be inserted into the receptacle 206 and connected both physically and electrically with the device 200 through the port 208. The disposable port 250 includes a strip port 252 that is configured to receive the test strip 150. When the port 250 is inserted into the receptacle 206, the surface with the port 252 is often flush with the surface 214, although other configurations are possible with respect to the position of the port 250 relative to the device 200.

FIG. 11 illustrates a view of an end of the device 200. FIG. 11 illustrates that port 208 and the printed circuit board 212 (or other suitable interface) are disposed therein at the end of the receptacle 206. The printed circuit board 212 may have traces 216 or other contacts on either side of the printed circuit board 212.

FIG. 12 illustrates a top view of the device 200, the port 250, and a test strip 150. In this example, the port 208 provides access to the contacts 216 of the printed circuit board 212. The port 250 also includes corresponding contacts 254 that are configured to connect with the traces 216. The contacts 254 may be spring arms, pins, and the like or any combination thereof. Further, the port 208 may be insert molded as previously described to provide an interface that is substantially impervious to contaminants. In this case, the port may be changeable to allow the device 200 to adapt to different form factors or to provide other functions according to the configuration of the port 250.

In this example, the port 250 also has a strip receptacle 260 (an example of the strip port 252) or strip port disposed on a side opposite the contacts 254, although the receptacle can be repositioned on any side of the port 250. The test strip 150 may be inserted into the receptacle 260 and a sample of the test strip 150 may be analyzed when the port 250 is connected to the port 208.

The port 250 in this example may include a first portion 256 and a second portion 258. The portion 256 and the portion 258 can be one integrated port or may include portions that can be repeatedly separated and connected. As previously mentioned, the portion 258 can be replace with differently configured portions to provide a receptacle 260 that accommodates different test strip form factors.

The portion 256 may be configured to interface with the device 200 via the port 208. The portion 256 may also include retention tabs 262 that interact with corresponding connectors 264 to connect at least the portion 256 with the device 200 physically. In one example, the portion 256 may permanently connect with the device 200, while allowing the portion 258 to be disposable. Advantageously, a user can select differently configured portions 258 to adapt to different configurations of the test strips. This may allow a user not only to replace the port 250 or a portion thereof, but also utilize test strips of different form factors.

FIG. 13 illustrates a perspective view of one embodiment of a disposable port 250. In this example, the port 250 includes a portion 256 that is configured to interface with test strips and a portion 258 that is configured to interface with a measurement device 200. The portion 256 includes spring arms 254 that are configured to connect with traces on a printed circuit board as previously disclosed. Alternatively, the portion 258 may include pin contacts or other contacts that interface with corresponding structure on the port 208 of the device 200 to establish the requisite connection.

The portion 256, in this example, includes a retention tab 262 that enables the port 250 to connect with the device 200 in a permanent or semi-permanent fashion. When connected to the device 200, the tab 262 keeps the portion 256 in place while the portion 258 can be separated from the portion 256 and replaced with a new portion or simply cleaned. As previously noted, the portion 258 can have multiple configurations to enable connectivity with different test strip form factors.

The port 250 includes a guide member 264, in this embodiment, that interacts with corresponding rail structure on the device 200 to facilitate insertion of the port 250 onto the device 200. The cooperation of the guide member 264 and the rail structure can ensure that the port 250 is properly aligned with the port 208 during insertion and can also prevent damage to the contacts during both insertion and/or removal of the port 250. This can prevent damage to the spring arms 264 and ensure that a proper connection is made between the port and the device.

FIG. 14 illustrates a perspective view of one embodiment of the portion 258. The portion 258 includes pins 266 that are used to connect with corresponding structure in the portion 256. The pins 266 may provide a friction fit with the corresponding structure to retain the connection between the portion 256 and the portion 258.

FIG. 15 illustrates a view of a test port or receptacle 260 of the portion 258. In this example, the portion 258 includes a receptacle 260 configured to receive a test strip. Contacts 270 are disposed inside the port and arranged to make at least electrical contact with the test strip in order to allow analysis of the blood sample on the strip.

FIG. 16 depicts a side view the device 200 with a disposable port 250 connected thereto. FIG. 16 illustrates the spring arms 264 inside of the portion 256. On the device side, the spring arms extent out of the port 250 and make contact with the printed circuit board 212 inside the device 200. The opposite end of the spring arms 264 form sockets 272. The sockets 272 are configured to receive and electrically connect with the pins 266 that extend out of the portion 258. The pins 266 also include contacts 270 (illustrated as spring arms in this example) inside of the portion 258 that are configured to electrically connect with a test strip 150 when the test strip inserted in the receptacle or port 260.

As previously stated, the portion 258 can be configured to adapt to multiple strip form factors. As a result, the portion 258 may also include contacts 270 that are configured as pins, plugs, sockets, clips, and the like or any combination thereof. The interface between the portion 256 and 258 allows at least the portion 256 to be replaceable when ever it begins to fail or is contaminated or for any other reason. Further, the electrical connections between the device 200, the portion 256, the portion 258, and the test strip 150 can take various forms including, but not limited to, pin contacts, clip pins, spring arms, and the like or any combination thereof. In this example, the contacts or pins illustrated for the portions 256 and 258 cooperate to establish electrical connects.

Figure 17A:
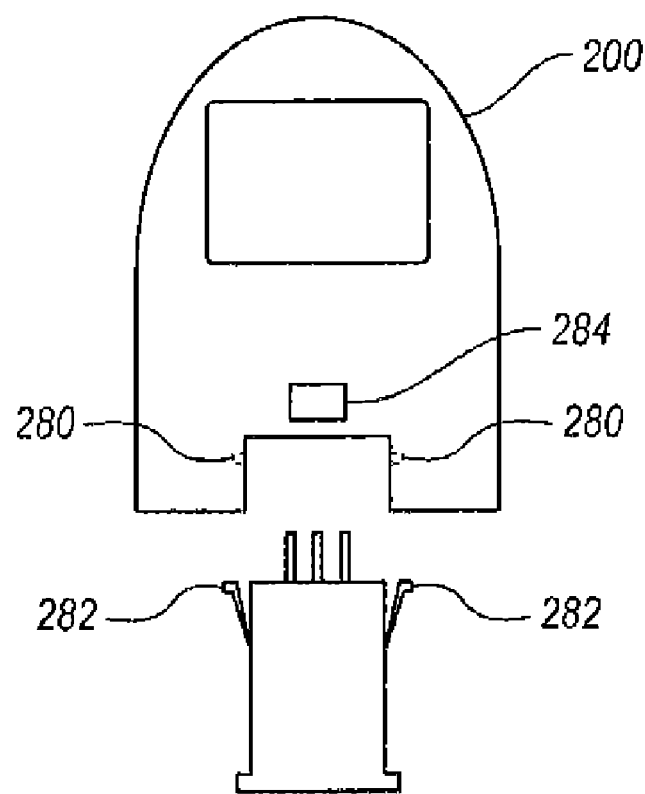
FIGS. 17A and 17B illustrate additional structure for associating the strip port with a measurement device.
Figure 17B:
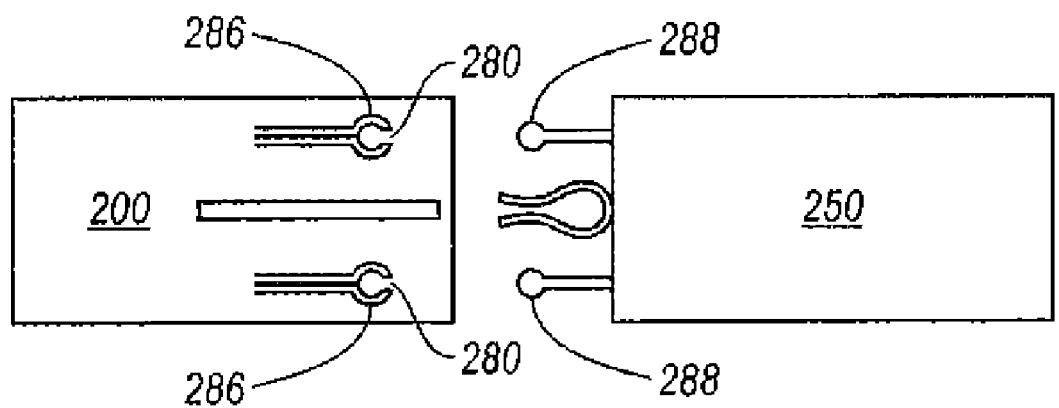

FIGS. 17A-B illustrates examples of the connections or associations between the port 250 and the device 200. FIG. 17A illustrates that the connection between the port and the device may include a latch 282 that interfaces with a receptacle 280 to secure the portion 258 to the device 200. The receptacle 280 and latch 282 cooperate to provide a connection. A release 284 may also be included in the device 200 that releases the latch 282 from the receptacle 280. As a result, the connection illustrated in FIG. 17A can be permanent or semi-permanent.

FIG. 17B illustrates another interface or connection between the device 200 and the port 250. In this example, the device may include sockets 286 that have an opening adapted to receive the ball 288 connected to the port 250. The ball 288, when snapped into the socket 286, expands the socket 286 to allow the ball 288 to enter the socket 286. Once the ball is inserted, the socket contracts to establish the connection. As a result, a force is required to insert the ball 288 into the socket. A similar force may be required to release the connection illustrated in FIG. 17B. In these examples, the connection may be semi-permanent and ensures that the electrical connection is maintained.

In other embodiments, the connection between the port 250 and the device 200 (or between the contact pins 266 and sockets 272) may include a press fit or a friction fit. For instance, the port 250 may be slightly wider than the receptacle 206. As the port 250 is inserted into the receptacle 206, the friction between the port 250 and the device 200 maintains the port in the proper position.

In other embodiments, the electrical connections can also provide the mechanical connection. For example, a friction fit between the pins 266 and the sockets 272 may provide sufficient force to keep the portions 256 and 258 connected. A user, however, can remove the portion 256 and replace it.

Certain embodiments relate to in vivo (e.g., continuous monitoring) systems. A continuous monitoring system typically includes a sensor that is worn or placed below the skin, a transmitter that collects glucose information from the sensor, and a receiver that collects the information from the transmitter. The sensor can collect glucose level information continuously, periodically, or at other intervals. Advantageously, a user is relieved from having to repeatedly lance his or her body to collect a blood sample once the sensor is inserted, although the sensor (e.g., an electrochemical sensor that is inserted into a body) can be replaced. U.S. Pat. No. 6,175,752, which is hereby incorporated by reference in its entirety, discloses additional examples of a continuous monitoring system.

Embodiments of the invention relate to components of a continuous monitoring system that may be replaceable. In one embodiment, the i between the sensor and the transmitter may become contaminated. The transmitter or sensor control unit, for example, may have an interface with the sensor that has been molded to form a barrier between the transmitter's contacts and circuitry internal to the transmitter. This allows the transmitter's contacts to be washed without damaging the transmitter's circuitry. Alternatively, the contacts may be included in a replaceable port that can be replaced as needed. Similarly, the interface on the sensor may be molded to form a barrier to contamination or be replaceable.

In these examples, the strip connectors or ports can be used with continuous monitoring systems. As discussed herein, the sensor control unit or transmitter typically has a port to interface with the sensor. This port can be molded such that the contacts can be cleaned to prolong the MTBF. Alternatively, the port can be replaceable and/or washable. A replaceable port allows the continuous system to adapt to different sensor form factors.

Embodiments of the invention further extend to kits. Examples of a kit include a measurement device with one or more strip connectors. In some kits, different strip connectors or ports for different types of strips may be included. This allows the measurement device to be used with different strip form factors. The kits may also include a plurality of test strips. In certain examples, the measurement device may be configured for use with disposable test strips as well as with test strips that are configured for continuous monitoring systems. Thus, the measurement device may include a receiver to receive information from a transmitter that collects glucose information from an inserted sensor. The measurement device may also include a strip connector, such as those disclosed herein, for use with single use test strips.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An analyte measuring device comprising:
   a housing comprising an interior;
   a receptacle positioned in the housing and configured to receive one of a plurality of removable sensor ports, wherein two surfaces of the receptacle abut with two corresponding surfaces of the removable sensor port when the removable sensor port is received within the receptacle; and
   circuitry disposed in the interior of the housing and configured to communicate with the plurality of removable sensor ports,
   wherein the circuitry is configured to receive and process one or more signals from the removable sensor port, the one or more signals being indicative of an analyte concentration in a sample.

2. The analyte measuring device of claim 1, wherein the receptacle is configured to engage the plurality of removable sensor ports by press fit engagement.

3. The analyte measuring device of claim 1, wherein the receptacle is configured to engage the plurality of removable sensor ports by snap fit engagement.

4. The analyte measuring device of claim 1, wherein the sensor ports of the plurality of sensor ports are disposable.

5. The analyte measuring device of claim 1, wherein the analyte is glucose.

6. The analyte measuring device of claim 1, wherein the removable sensor port is configured to receive an analyte sensor.

7. The analyte measuring device of claim 1, further comprising a user interface.

8. The analyte measuring device of claim 1, further comprising a display disposed on the housing and configured to display the analyte concentration to a user of the analyte measuring device.

9. The analyte measuring device of claim 8, wherein the display is a liquid crystal display (LCD) or a light emitting diode (LED) display.

10. The analyte measuring device of claim 8, wherein the display is configured to provide instructions to a user of the analyte measuring device.

11. The analyte measuring device of claim 8, wherein the analyte is glucose, and wherein the display comprises an indicator activatable when the glucose concentration of the sample indicates hyperglycemia, hypoglycemia, impending hyperglycemia, or impending hypoglycemia.

12. The analyte measuring device of claim 8, wherein the display is configured to display a graph of analyte concentration over time.

13. The analyte measuring device of claim 8, wherein the display is a touch screen display.

14. The analyte measuring device of claim 13, wherein the touch screen display is configured for data entry by the user.

15. The analyte measuring device of claim 1, wherein the plurality of removable sensor ports comprises at least a first sensor port configured to receive a first sensor having a first sensor configuration and at least a second sensor port configured to receive a second sensor having a second sensor configuration.

16. The analyte measuring device of claim 15, wherein the first and second sensors are first and second test strips respectively.

17. The analyte measuring device of claim 1, comprising a member of the plurality of removable sensor ports, and further comprising an interface formed between the housing and the member of the plurality of removable sensor ports, the interface providing a barrier that is substantially or completely impervious to liquids.

18. The analyte measuring device of claim 17, wherein the interface comprises a press fit.

19. The analyte measuring device of claim 17, wherein the interface comprises a snap fit.

20. The analyte measuring device of claim 1, wherein the circuitry is configured to determine a dosage of medication based at least in part on the one or more signals.

21. The analyte measuring device of claim 20, wherein the analyte is glucose and the medication is insulin.

22. The analyte measuring device of claim 20, further comprising a display disposed on the housing and configured to display the analyte concentration to a user of the analyte measuring device, wherein the display is further configured to display the determined dosage of medication.

23. The analyte measuring device of claim 22, wherein the analyte measuring device is configured to communicate with a drug delivery device and/or system.

24. The analyte measuring device of claim 1, wherein the housing is injection molded.

25. The analyte measuring device of claim 1, wherein the circuitry is electrically coupled to the removable sensor port via pin contacts.

26. The analyte measuring device of claim 1, wherein the circuitry is electrically coupled to the removable sensor port via spring arms.

27. The analyte measuring device of claim 1, wherein the circuitry is electrically coupled to the removable sensor port via clips.

28. The analyte measuring device of claim 1, wherein the circuitry is electrically coupled to the removable sensor port via gold-plated high strength steel.

29. The analyte measuring device of claim 1, further comprising a receiver configured to receive analyte concentration related information from a transmitter which receives the information from an implanted analyte sensor.

30. The analyte measuring device of claim 29, wherein the receiver is a wireless receiver.

31. The analyte measuring device of claim 30, wherein the receiver utilizes a radio frequency (RF) protocol.

32. The analyte measuring device of claim 1, wherein the circuitry is configured to determine trending of analyte concentration.

33. The analyte measuring device of claim 32, wherein the trending provides for a rate and/or acceleration of analyte concentration increase or decrease.

34. A glucose measuring device comprising
a housing comprising an interior;
a receptacle positioned in the housing and configured to receive one of a plurality of removable sensor ports, wherein two surfaces of the receptacle abut with two corresponding surfaces of the removable sensor port when the removable sensor port is received within the receptacle;
circuitry disposed in the interior of the housing and configured to communicate with the plurality of removable sensor ports,
wherein the circuitry is configured to receive and process one or more signals from the removable sensor port, the one or more signals being indicative of a glucose concentration in a sample;
a display disposed on the housing and configured to display the glucose concentration to a user of the glucose measuring device; and
a member of the plurality of removable sensor ports.

35. The glucose measuring device of claim 34, wherein the display is a liquid crystal display (LCD) or a light emitting diode (LED) display.

36. The glucose measuring device of claim 34, wherein the receptacle engages the member of the plurality of removable sensor ports by press fit engagement or snap fit engagement.

37. The glucose measuring device of claim 34, wherein the member of the plurality of removable sensor ports is disposable.

38. The glucose measuring device of claim 34, wherein the removable sensor port is configured to receive a glucose sensor.

39. The glucose measuring device of claim 34, wherein the display is configured to provide instructions to a user of the glucose measuring device.

40. The glucose measuring device of claim 34, wherein the housing is injection molded.

41. The glucose measuring device of claim 34, wherein the circuitry is electrically coupled to the removable sensor port via pin contacts, spring arms, or clips.

42. The glucose measuring device of claim 34, wherein the circuitry is electrically coupled to the removable sensor port via gold-plated high strength steel.

43. The glucose measuring device of claim 34, wherein the display comprises an indicator activatable when the glucose concentration of the sample indicates hyperglycemia, hypoglycemia, impending hyperglycemia, or impending hypoglycemia.

44. The glucose measuring device of claim 34, wherein the circuitry is configured to determine trending of glucose concentration.

45. The glucose measuring device of claim 34, wherein the trending provides for a rate and/or acceleration of glucose concentration increase or decrease.

46. The glucose measuring device of claim 34, wherein the display is configured to display a graph of glucose concentration over time.

47. The glucose measuring device of claim 34, wherein the display is a touch screen display.

48. The glucose measuring device of claim 47, wherein the touch screen display is configured for data entry by the user.

49. The glucose measuring device of claim 34, wherein the plurality of removable sensor ports comprises at least a first sensor port configured to receive a first glucose sensor having a first glucose sensor configuration and at least a second sensor port configured to receive a second glucose sensor having a second glucose sensor configuration.

50. The glucose measuring device of claim 49, wherein the first and second glucose sensors are first and second glucose test strips respectively.

51. The glucose measuring device of claim 34, further comprising an interface formed between the housing and the member of the plurality of removable sensor ports, the interface providing a barrier that is substantially or completely impervious to liquids.

52. The glucose measuring device of claim 51, wherein the interface comprises a press fit or a snap fit.

53. The glucose measuring device of claim 34, wherein the circuitry is configured to determine a dosage of medication based at least in part on the one or more signals.

54. The glucose measuring device of claim 53, wherein the medication is insulin.

55. The glucose measuring device of claim 53, wherein display is configured to display the determined dosage of medication.

56. The glucose measuring device of claim 55, wherein the glucose measuring device is configured to communicate with a drug delivery device and/or system.

57. The glucose measuring device of claim 34, wherein the glucose measuring device further comprises a receiver configured to receive glucose concentration related information from a transmitter which receives the information from an implanted glucose sensor.

58. The glucose measuring device of claim 57, wherein the receiver is a wireless receiver.

59. The glucose measuring device of claim 58, wherein the receiver utilizes a radio frequency (RF) protocol.

60. An analyte measuring device comprising:
a housing comprising an interior;
a receptacle positioned in the housing and configured to receive one of a plurality of removable sensor ports, wherein two surfaces of the receptacle abut with two corresponding surfaces of the removable sensor port when the removable sensor port is received within the receptacle, and wherein one surface of the removable sensor port is flush with the housing;
circuitry disposed in the interior of the housing and configured to communicate with the plurality of removable sensor ports,
wherein the circuitry is configured to receive and process one or more signals from the analyte sensor, the one or more signals being indicative of an analyte concentration in a sample; and
a display disposed on the housing and configured to display the analyte concentration to a user of the analyte measuring device.

61. An analyte measuring device comprising:
a housing comprising an interior;
a receptacle positioned in the housing and configured to receive one of a plurality of removable sensor ports, wherein the plurality of removable sensor ports comprises at least a first sensor port configured to receive a first sensor having a first sensor configuration and at least a second sensor port configured to receive a second sensor having a second sensor configuration; and
circuitry disposed in the interior of the housing and configured to communicate with the plurality of removable sensor ports, wherein the circuitry is configured to receive and process one or more signals from the analyte sensor, the one or more signals being indicative of an analyte concentration in a sample.

62. The analyte measuring device of claim 61, wherein the first and second sensors are first and second test strips respectively.

63. A glucose measuring device comprising
a housing comprising an interior;
a receptacle positioned in the housing and configured to receive one of a plurality of removable sensor ports, wherein the plurality of removable sensor ports comprises at least a first sensor port configured to receive a first glucose sensor having a first glucose sensor configuration and at least a second sensor port configured to receive a second glucose sensor having a second glucose sensor configuration;
circuitry disposed in the interior of the housing and configured to communicate with the plurality of removable sensor ports, wherein the circuitry is configured to receive and process one or more signals from the glucose sensor, the one or more signals being indicative of a glucose concentration in a sample;
a display disposed on the housing and configured to display the glucose concentration to a user of the glucose measuring device; and
a member of the plurality of removable sensor ports.

64. The glucose measuring device of claim 63, wherein the first and second glucose sensors are first and second glucose test strips respectively.

* * * * *